(12) United States Patent
Bao et al.

(10) Patent No.: US 11,097,253 B2
(45) Date of Patent: Aug. 24, 2021

(54) CATALYST AND METHOD FOR PREPARING LIQUID FUEL AND LIGHT OLEFINS BY DIRECT CONVERSION OF SYNGAS

(71) Applicant: DALIAN INSTITUTE OF CHEMICAL PHYSICS, CHINESE ACADEMY OF SCIENCES, Liaoning (CN)

(72) Inventors: Xinhe Bao, Liaoning (CN); Feng Jiao, Liaoning (CN); Xiulian Pan, Liaoning (CN)

(73) Assignee: DALIAN INSTITUTE OF CHEMICAL PHYSICS, CHINESE ACADEMY OF SCIENCES, Liaoning (CN)

( * ) Notice: Subject to any disclaimer, the term of this patent is extended or adjusted under 35 U.S.C. 154(b) by 0 days.

(21) Appl. No.: 16/618,749

(22) PCT Filed: Aug. 2, 2018

(86) PCT No.: PCT/CN2018/098378
§ 371 (c)(1),
(2) Date: Feb. 26, 2020

(87) PCT Pub. No.: WO2018/219364
PCT Pub. Date: Dec. 6, 2018

(65) Prior Publication Data
US 2020/0276559 A1 Sep. 3, 2020

(30) Foreign Application Priority Data
Jun. 2, 2017 (CN) .......................... 201710408016.X

(51) Int. Cl.
| | | |
|---|---|---|
| *B01J 23/06* | (2006.01) | |
| *B01J 23/00* | (2006.01) | |
| *B01J 23/10* | (2006.01) | |
| *B01J 23/26* | (2006.01) | |
| *B01J 23/34* | (2006.01) | |
| *B01J 29/40* | (2006.01) | |
| *B01J 29/48* | (2006.01) | |
| *B01J 37/04* | (2006.01) | |
| *C10G 2/00* | (2006.01) | |

(52) U.S. Cl.
CPC ............ *B01J 23/06* (2013.01); *B01J 23/005* (2013.01); *B01J 23/10* (2013.01); *B01J 23/26* (2013.01); *B01J 23/34* (2013.01); *B01J 29/405* (2013.01); *B01J 29/48* (2013.01); *B01J 37/04* (2013.01); *C10G 2/334* (2013.01); *C10G 2400/02* (2013.01); *C10G 2400/20* (2013.01); *C10G 2400/26* (2013.01)

(58) Field of Classification Search
CPC ............... C10G 2/334; C10G 2400/20; C10G 2400/02; C10G 2400/26; B01J 23/34; B01J 23/06; B01J 23/005; B01J 23/10; B01J 29/40; B01J 37/04; B01J 29/405; B01J 29/48; C07C 11/06; C07C 1/043; C07C 2529/40
See application file for complete search history.

(56) References Cited

U.S. PATENT DOCUMENTS

| | | | | |
|---|---|---|---|---|
| 2011/0201860 A1* | 8/2011 | Akhtar | ................. | C07C 2/76 585/419 |
| 2016/0176776 A1* | 6/2016 | Ilias | ................. | B01J 35/023 585/408 |

FOREIGN PATENT DOCUMENTS

| | | |
|---|---|---|
| CA | 2891248 A1 | 5/2014 |
| CN | 101396662 A | 4/2009 |
| CN | 106311317 A | 1/2017 |
| CN | 106345514 A | 1/2017 |
| WO | 2016105888 A1 | 6/2016 |

OTHER PUBLICATIONS

Zhang et al., "Preparation and Characterization of Fe/AC Catalysts for Synthesis of Light Olefins via Carbon Monoxide Hydrogenation"; Chinese Journal of Catalysis; vol. 24 No. 4, Apr. 2003.
Galvis et al., "Effects of sodium and sulfur on catalytic performance of supported iron catalysts for the Fischer-Tropsch synthesis of lower olefins", Journal of Catalysis, vol. 303 (2013), pp. 22-30.
Shen et al., "Studies on Highly Dispersed Iron/Activated Carbon Catalysts for Fischer-Tropsch Synthesis"; Journal of Fuel Chemistry and Technology; vol. 19, No. 4, Dec. 1991, pp. 289-296.
Ma et al., "Non-Anderson-Schulz-Flory Product Distribution of Fischer-Tropsch Synthesis over Iron/Activated Charcoal Catalyst"; Chinese Journal of Catalysis; vol. 22, No. 3 May 2001, pp. 279-282.
Mao et al., "Highly effective hybrid catalyst for the direct synthesis of dimethyl ether from syngas with magnesium oxide-modified HZSM-5 as a dehydration component"; Journal of Catalysis; vol. 230 (2005), pp. 140-149.
Xu et al., "Synthesis of dimethyl ether (DME) from methanol over solid-acid catalysts", Applied Catalysis A: General; vol. 149 (1997), pp. 289-301.
Erena et al., "Conversion of syngas to liquid hydrocarbons over a two-component (Cr2O3—ZnO and ZSM-5 zeolite) catalyst: Kinetic modelling and catalyst deactivation", Chemical Engineering Science; 55 (2000) pp. 1845-1855.

(Continued)

Primary Examiner — Jafar F Parsa
(74) Attorney, Agent, or Firm — Novick, Kim & Lee, PLLC; Allen Xue

(57) ABSTRACT

Direct conversion of syngas produces liquid fuels and light olefins. The catalytic reaction is conducted on a fixed bed or a moving bed. The catalyst comprises A and B components. The component A is composed of active metal oxides, and the active ingredients of the component B are zeolites with a MEL structure. The distance between the geometric centers of catalyst A and catalyst B particles is 2 nm-10 mm; a weight ratio of the catalyst A to the catalyst B is 0.1-20. The pressure of the syngas is 0.1-10 MPa; reaction temperature is 300-600° C.; and space velocity is 300-10000 $h^{-1}$. The reaction mainly produces gasoline with high octane number, and co-generates light olefins. Meanwhile, the selectivity for a methane byproduct is low (less than 10%).

19 Claims, No Drawings

(56) References Cited

OTHER PUBLICATIONS

Erena et al.; "Study of the preparation and composition of the metallic function for the selective hydrogenation of CO2 to gasoline over bifunctional catalysts"; Journal of Chemical Technology and Biotechnology; 78:161-166 (online: 2003) DOI: 10.1002/jctb.720.
Park et al.; "Direct conversion of synthesis gas to light olefins using dual bed reactor"; Journal of Industrial and Engineering Chemistry; vol. 15 (2009), pp. 847-853.

* cited by examiner

CATALYST AND METHOD FOR PREPARING LIQUID FUEL AND LIGHT OLEFINS BY DIRECT CONVERSION OF SYNGAS

TECHNICAL FIELD

The present invention belongs to preparation of liquid fuel and light olefins from syngas, and particularly relates to a catalyst and a method for preparing liquid fuel and light olefins using direct conversion of syngas.

BACKGROUND

With the development of the economy and the improvement of living standards, the demands for liquid fuel and chemicals are also increased sharply year by year. At present, the gasoline is produced mainly by catalytic reforming of heavy naphtha. With the consumption of global oil resources and the high price of crude oil, for countries especially like China with a shortage of oil resources, more than 60% of the consumption of oil relies on imports every year. It has important social significance and strategic significance to seek an alternative technological route to develop and use a method for preparing light olefin from non-oil-based carbon resources such as coal, biomass and the like.

China has rich coal resources. The simple technical route of using coal as the raw material, gasifying to obtain synthesis gas (i.e., mixed gas of CO and $H_2$), converting the synthesis gas into methanol, and preparing the methanol into gasoline by dimethyl ether is mature and is already industrialized. The route provides an important new route for preparing liquid fuel by carbon resources such as coal and natural gas. However, if a direct route of direct conversion of syngas is realized without methanol synthesis and methanol dehydration for preparing dimethyl ether, not only the process flow can be simplified, but also unit operation can be reduced and investment and energy consumption can be reduced. The traditional Fischer-Tropsch path can prepare the liquid fuel through direct conversion of syngas. However, limited by the reaction mechanism, CO and $H_2$ molecules are dissociated and absorbed on the surface of the catalyst to produce surface C atoms and O atoms. The C atoms and the O atoms react with hydrogen absorbed on the surface of the catalyst to form a methylene ($CH_2$) intermediate while releasing water molecules. The $CH_2$ intermediate is freely polymerized on the surface of the catalyst by a migratory insertion reaction to produce hydrocarbon products having different number of carbon atoms (from one to thirty, and sometimes even hundreds of carbon atoms). In the whole reaction, the carbon atoms of the hydrocarbon products are widely distributed, and the selectivity of target products is low. For example, the selectivity of the gasoline is lower than 50%.

Light olefins mainly include ethylene, propylene and butene, and are the foundation of the modern chemical industry. At present, the light olefins are mainly prepared by naphtha cracking. A multi-step and multi-reactor technology of obtaining syngas from coal gasification, converting the syngas into methanol or dimethyl ether, and converting the methanol or dimethyl ether into light olefins is relatively mature, and is already industrialized. To simplify the reaction technology and shorten the technical route, catalysts based on the traditional Fischer-Tropsch reaction, such as Fe-based catalyst, are modified and improved. The selectivity of the light olefins can be effectively improved by adding additives with different components such as alkalis K and Na and transition metal Mn, Cu, etc. Ruhy Chemical Corporation of Germany develops a Fe—Zn—Mn—K catalyst promoted with multicomponent auxiliaries to synthesize light olefin [12]. Zhang Jingchang et. al from Beijing University of Chemical Technology report a Fe—Mn—K/AC catalyst with ferric oxalate as precursor. The CO conversion rate is as high as 97% at space velocity of 600 $h^{-1}$, 15 bars and 320° C.; and the selectivity of $C_2^=$-$C_4^=$ in hydrocarbon is 68% [Zhang Jingchang, Wei Guobin, Cao Weiliang, Chinese Journal of Catalysis 24(2003)259-264] and exceeds the selectivity of $C_2$-$C_4$ hydrocarbon predicted by ASF distribution model. A carrier of the catalyst also has an important modification role in product selectivity through interaction with Fe species. De Jong research group from Holland recently reports a 12 wt % of Fe catalyst prepared by using carbon nanofiber (CNF) and $\alpha$-$Al_2O_3$ as carriers and ferric ammonium citrate as a precursor. Under conditions of low pressure (1 bar), 350° C. and $H_2$/CO=1, the reaction is conducted for 15 hours; the CO conversion rate is 0.5%-1.0%; and the selectivity of light olefin in hydrocarbon is 60% [H. M. T. Galvis, J. H. Bitter, C. B. Hhare, M. Ruitenbeek, A. L. Dugulan, K. P. de Jong, Science 335 (2012) 835-838]. Similarly, under conditions of 340° C., $H_2$/CO=1, 20 bars and space velocity of 1500 $h^{-1}$, the catalyst obtains conversion rate of 70%-88%; FTY are respectively $2.98 \times 10^{-5}$ mol CO/gFe·s and $1.35 \times 10^{-5}$ mol CO/gFe·s; and the selectivity of $CO_2$ is 42%-46%, wherein the selectivity of light olefin in hydrocarbon is 52%-53%. Later, they discover that a small amount of 0.03% of S and about 0.2% of Na in the catalyst have an obvious promotion role in the reaction activity and the selectivity of the light olefin [H. M. T. Galvis, A. C. J. Koeken, J. H. Bitter, T. Davidian, M. Ruitenbeek, A. I. Dugulan, K. P. de Jong, J. Catal. 303 (2013) 22-30]. Dalian Institute of Chemical Physics of Chinese Academy of Sciences systematically and deeply researches the carrier of activated carbon, and finds that the product on an iron catalyst loaded by the activated carbon deviates from ASF distribution [Shen Jianyi, Lin Liwu, Zhang Su, and Liang dongBai, Journal of Fuel Chemistry and Technology 19 (1991) 289-297; Ma Wenping, Ding Yunjie, Luo Hongyuan, et al., Chinese Journal of Catalysis, 22 (2001)279-282]. In addition, the preparation method and technology of the catalyst, such as calcination process and reduction condition, may directly affect the dispersion and the size of active components, thereby regulating the activity of reaction and the selectivity of product. Beijing University of Chemical Technology prepares a nano-scale Fe-based catalyst by using a supercritical fluid combination technology (i.e., chemical precipitation, gel, and supercritical drying methods) to highly disperse the active component Fe and auxiliaries. The CO conversion rate is greater than 96%, and the selectivity of light olefin in the hydrocarbon is greater than 54%. [Beijing University of Chemical Technology; A nano catalyst for preparing light olefin from synthesis gas and a preparation method: China, 101396662 [P]. 2009-Apr. 1].

To this end, researchers try to couple multiple processes and make a large number of attempts. Xu et al. mix CuO—ZnO—$Al_2O_3$ with ZSM-5 to obtain a catalyst, wherein products obtained in the conversion reaction of the synthesis gas mainly include dimethyl ether [M. Xu, J. H. Lunsford, D. W. Goodman, A. Bhattacharyya, Appl. Catal. A. General 149 (1997) 289; D. Mao, W. Yang, J. Xia, B. Zhang, Q. Song, Q. Chen, J. Catal. 230 (2005) 140]. Erena et al. mix multicomponent metal composites such as CuO/ZnO/$Al_2O_3$ and the like with ZSM-5 molecular sieve to catalyze the conversion of the synthesis gas. The obtained products mainly include gasoline. [J. Erena, J. M. Arandes, J. Bilbao, A. G. Gayubo, H. I. De Lasa, Chemical Engineering Science 2000, 55, 1845; J. Erena, J. M. Arandes, R. Garona, A. G. Gayubo, J. Bilbao, Journal of Chemical Technology and Biotechnology 2003, 78, 161]. Park et al. cracked a large number of $C_{5+}$ products into light olefins by firstly conducting the Fischer-Tropsch reaction in a first reactor on Fe—Cu—Al catalyst at 300° C., 10 atm ad GHSV=3600 $h^{-1}$ and then cracking a catalyst bed by ZSM-5 at 500° C. in a second reactor by means of a dual bed reactions. The selectivity of the light hydrocarbon in the obtained hydrocarbon product is 52%, and the selectivity of the light olefins in the whole product is 28% [J. L. Park, Y. J. Lee, K. W. Jun, J. W. Bae, N. Viswanadham, Y. H. Kim, J. Ind. Eng. Chem. 15 (2009) 847-853].

SUMMARY OF INVENTION

In view of the above problems, the present invention provides a catalyst and a method for preparing liquid fuel and light olefins using direct conversion of syngas. The invented catalyst can catalyze direct conversion of the syngas to generate liquid fuel and light olefins. The selectivity of gasoline fraction can reach 50-80%.

The technical solution of the present invention is as follows:

A catalyst is provided. The catalyst is a composite catalyst A+B; the active ingredient of the component A is an active metal oxide; the component B is a zeolite having MEL structure; the active metal oxide is one or more than one of MnO, $MnCr_2O_4$, $MnAl_2O_4$, $MnZrO_4$, ZnO, $ZnCr_2O_4$, $ZnAl_2O_4$, $CeO_2$, $CoAl_2O_4$ and $FeAl_2O_4$.

The catalyst component A is preferably one or more than one of MnO, $Cr_2O_3$, $MnCr_2O_4$, $MnAl_2O_4$, $MnZrO_4$, $ZnAl_2O_4$, $CeO_2$, $CoAl_2O_4$ and $FeAl_2O_4$, and more preferably one or more than one of MnO, $Cr_2O_3$, $MnCr_2O_4$, $MnAl_2O_4$, $MnZrO_4$, $CeO_2$, $CoAl_2O_4$ and $FeAl_2O_4$.

The zeolite having MEL structure in the catalyst component B is composed of H, O, Si and Al; the component B can also comprise one or more than one of dispersing agents of $Al_2O_3$, graphite, $SiO_2$, $ZrO_2$, $TiO_2$, $Cr_2O_3$, $Ga_2O_3$, CaO, MgO, $CeO_2$, $In_2O_3$ and $SnO_2$; and the content of the dispersing agents is 0-50% wt.

A distance between geometric centers of the active metal oxide of the component A and the particle of the component B is 20 nm-10 mm, preferably 50 nm-1 mm and more preferably 100 nm-0.5 mm.

A weight ratio of the active ingredients in the component A to the component B is within a range of 0.1-20 times, and preferably 0.3-5.

The active metal oxide is composed of crystals with a size of 5-30 nm, and a large amount of oxygen vacancies exist within a distance range of depth 0.3 nm from the surfaces of the crystals to the internal direction of the crystals; based on the oxygen molar content of 100% in theoretical stoichiometric ratio, the percent concentration of surface oxygen vacancies is defined as (100%—the percent of molar weight of oxygen atoms in the oxygen molar content in theoretical stoichiometric ratio); and the oxygen vacancy concentration is preferably 20-90%, more preferably 40-90% and most preferably 50-90%.

A dispersing agent is also added to the catalyst A; the dispersing agent is one or two of $Al_2O_3$, $Cr_2O_3$, $ZrO_2$ and $TiO_2$; the active metal oxide is dispersed in the dispersing agent; and the content of the dispersing agent in the catalyst A is 10-90 wt %, and the balance is the active metal oxide.

A method for preparing liquid fuel co-generated light olefins using direct conversion of syngas is provided. Syngas is used as reaction raw material; and a conversion reaction is conducted on a fixed bed or a moving bed.

The pressure of the syngas is 0.1-10 MPa, preferably 1-8 MPa and more preferably 2-8 MPa; reaction temperature is 300-600° C., and preferably 300° C.-500° C.; and space velocity is 300-10000 $h^{-1}$.

The syngas used in the reaction is $H_2$/CO mixture, and the ratio of $H_2$/CO is 0.2-3.5, and preferably 0.3-2.5.

The liquid fuel is mainly gasoline, is mainly composed of iso-hydrocarbon with high octane number, and co-generates light olefins. The light olefins refer to $C_2$-$C_4$ olefins having 2 to 4 carbon atoms, comprising one or more than one of ethylene, propylene and butene.

The present invention has the following advantages:

1. Different from the traditional technology for preparing the gasoline through methanol (MTG for short), this technology realizes preparation of liquid fuel and light olefins through one-step direct conversion of the syngas.

2. The selectivity of the gasoline fraction in the product is high and can reach 50-80%. The other products are mainly light olefins with high added value, and the selectivity of the light olefins can reach 10-30%.

3. Compared with the traditional Fischer-Tropsch synthesis technology, the gasoline composition comprises a large amount of isoparaffins hydrocarbons with high octane number; the linear hydrocarbons have low selectivity and therefore high oil quality; and the selectivity of the methane byproduct is low, which is less than 10%.

4. The composite catalyst in the patent is simple in preparation process and mild in conditions. The reaction process has an extremely high product yield and selectivity, and has excellent application prospect.

DETAILED DESCRIPTION

The present invention is further illustrated below by embodiments, but the scope of claims of the present invention is not limited by the embodiments. Meanwhile, the embodiments only give some conditions for achieving the purpose, but it doesn't mean that the conditions must be satisfied to achieve the purpose.

Embodiment 1

I. Preparation of Catalyst A (I) Synthesizing ZnO material with polar surface through an etching method:

(1) 0.446 g (1.5 mmol) of $Zn(NO_3)_2 \cdot 6H_2O$ and 0.480 g (12 mmol) of NaOH are weighed; 30 ml of deionized water is weighed and added to the material, and stirred for a time greater than 0.5 h to uniformly mix a solution; the temperature is increased to 160° C. with the reaction time of 20 h; precipitate is decomposed into zinc oxide, and naturally cooled to room temperature; reaction liquid is centrifugally separated to collect the centrifugally separated precipitate; and the precipitate is washed with deionized water twice to obtain ZnO oxide;

(2) an etching agent, such as oleic acid, hexamethylenetetramine, ethylenediamine, ammonia and hydrazine hydrate are ultrasonically mixed with ZnO oxide uniformly under normal temperature; the ZnO oxide is immersed in the solution of the etching agent; and a complexing or direct reduction reaction is formed by the etching agent and the zinc oxide; the above suspended matter is heated; then the suspended matter is taken out for washing and filtering the suspended matter to obtain active nano ZnO material having a large amount of surface oxygen holes.

In Table 1: the mass ratio of the catalyst to the etching agent is 1:3. The mass ratio of the oleic acid to the hexamethylenetetramine is 1:1, without solvent. The mass ratio of the oleic acid (5 wt %) to the hydrazine hydrate is 95:5, without solvent. Specific treatment conditions include the etching agent, temperature, treatment time and atmosphere types as shown in Table 1 below.

(3) Drying or Drying and Reducing:

After centrifuging or filtering the above obtained products and washing the products with deionized water, the products are dried, or dried and restored in an atmosphere which is inert gas or a gas mixture of inert gas and a reducing atmosphere, wherein the inert gas is one or more than one of $N_2$, He and Ar, the reducing atmosphere is one or more than one of $H_2$ and CO; a volume ratio of the inert gas to the reducing gas in the dried and restored gas mixture is 100/10-0/100, the temperature of drying and restoring is 350° C., and time is 4 h. ZnO material with abundant oxygen vacancies on the surface is obtained. Specific samples and preparation conditions thereof are shown in Table 1 below. The surface oxygen vacancy concentration is defined as: (100%-percent of the molar weight of oxygen atoms in theoretical stoichiometric ratio of oxygen molar content).

Corresponding products are defined as MnO 1-3.

(III) Synthesizing $CeO_2$ material with polar surface through an etching method: the preparation process is the same as that of the above (I). The difference is that, the precursor of Zn is changed for the corresponding precursor of Ce, which is one of cerium nitrate, cerium chloride and cerous acetate.

The etching process is the same as the preparation processes of products ZnO 3, ZnO 4 and ZnO 8 in step (2) in above (I). The catalyst having a great number of surface oxygen vacancies is synthesized. The surface oxygen vacancies are 67%, 38% and 25%.

Corresponding products are defined as CeO 1-3.

(IV) Synthesizing $Cr_2O_3$ material with polar surface through an etching method:

the preparation process is the same as that of the above (I). The difference is that, the precursor of Zn is changed for the corresponding precursor of Cr, which is one of chromic nitrate, chromium chloride and chromic acetate.

The etching process is the same as the preparation processes of products ZnO 3, ZnO 4 and ZnO 8 in step (2) in above (I). The catalyst having a great number of surface oxygen vacancies is synthesized. The surface oxygen vacancies are 45%, 29% and 20%.

TABLE 1

Preparation of ZnO Material and Parameter Performance

| Sample Number | Etching Agent | Temperature (° C.) and Carrier Gas (V/V) | Time/Minute | Drying or Drying and Reducing Temperature/° C. and Atmosphere | Surface Oxygen Vacancy Concentration |
|---|---|---|---|---|---|
| ZnO 1 | oleic acid-hexamethylenetetramine | 100, $N_2$ | 30 | 30, $N_2$ | 21% |
| ZnO 2 | oleic acid | 100, 5% $H_2/N_2$ | 30 | 300, 5% $H_2/N_2$ | 45% |
| ZnO 3 | oleic acid | 120, 5% CO/Ar | 60 | 350, 5% CO/Ar | 73% |
| ZnO 4 | oleic acid-5 wt % hydrazine hydrate | 140, 5% $H_2$/Ar | 60 | 310, 5% $H_2$/Ar | 67% |
| ZnO 5 | ethylenediamine | 100, 5% $NH_3$/Ar | 30 | 250, 5% $NH_3$/Ar | 30% |
| ZnO 6 | ethylenediamine | 140, 5% NO/Ar | 90 | 150, 5% NO/Ar | 52% |
| ZnO 7 | 20 wt % ammonium hydroxide | 100, Ar | 30 | 120, 5% CO/Ar | 22% |
| ZnO 8 | 20 wt % ammonium hydroxide | 140, 5% $NH_3$/5% NO/Ar | 90 | 400, He | 29% |

The surface oxygen vacancies are the percent of the molar weight of oxygen atoms in theoretical stoichiometric ratio of oxygen molar content within a distance range of depth 0.3 nm from the surfaces of the crystals to the internal direction of the crystals.

As a reference example, ZnO 9 which is not etched in step (2) and has no oxygen vacancy on the surface; and metal Zn 10 by completely reducing Zn.

(II) Synthesizing MnO material with polar surface through an etching method: the preparation process is the same as that of the above (I). The difference is that, the precursor of Zn is changed for the corresponding precursor of Mn, which is one of manganous nitrate, manganese chloride and manganese acetate.

The etching process is the same as the preparation processes of products ZnO 3, ZnO 5 and ZnO 8 in step (2) in above (I). The catalyst having a great number of surface oxygen vacancies is synthesized. The surface oxygen vacancies are 56%, 36% and 27%.

Corresponding products are defined as $Cr_2O_3$ 1-3.

(V) Synthesizing nano $ZnCr_2O_4$, $ZnAl_2O_4$, $MnCr_2O_4$, $MnAl_2O_4$ and $MnZrO_4$ spinel with high specific surface area and high surface energy:

zinc nitrate, aluminum nitrate, chromic nitrate, manganous nitrate and zirconium nitrate are adopted as precursors, and mixed with urea at room temperature in water; the above mixed liquid is aged; then the mixed liquid is taken out for washing, filtering and drying; and the obtained solid is roasted under an air atmosphere to obtain spinel oxide which grows along the (110) crystal plane direction. The sample is also treated by the etching method to synthesize the catalyst with a great number of surface oxygen vacancies. The etching process and aftertreatment process are the same as step (2) and step (3) in above (I). The sample has large specific surface area and many surface defects, and can be applied to catalyzing the conversion of syngas.

Specific samples and preparation conditions thereof are shown in Table 2 below. Similarly, the surface oxygen vacancies are defined as: (1-percent of the molar weight of oxygen atoms in theoretical stoichiometric ratio of oxygen molar content).

TABLE 2

Preparation of Spinel Material and Performance Parameters

| Sample Number | Stoichiometric Ratio of Metal Elements in Spinel and Final Molar Concentration of Metal in Water (mmol/L) | Aging Temperature ° C. and Time h | Roasting Temperature ° C. and Time h | Etching Agent, Temperature/° C., Atmosphere and Time/min | Surface Oxygen Vacancy |
|---|---|---|---|---|---|
| spinel 1 | ZnCr = 1:2, Zn is 50 mM | 120, 24 | 600, 48 | oleic acid, 120, 5% $H_2$/Ar, 60 | 41% |
| spinel 2 | ZnAl = 1:2, Zn is 50 mM | 130, 20 | 700, 24 | oleic acid, 120, 5% $H_2$/Ar, 60 | 72% |
| spinel 3 | MnCr = 1:2, Mn is 50 mM | 140, 18 | 750, 16 | oleic acid, 120, 5% $H_2$/Ar, 60 | 83% |
| spinel 4 | MnAl = 1:2, Mn is 50 mM | 145, 16 | 800, 10 | oleic acid, 120, 5% $H_2$/Ar, 60 | 20% |
| spinel 5 | MnZr = 1:2, Mn is 50 mM | 150, 12 | 900, 3 | oleic acid, 120, 5% $H_2$/Ar, 60 | 24% |

(V) Synthesizing nano $FeAl_2O_4$, $CoAl_2O_4$ and spinel with high specific surface area and high surface energy: the preparation process is the same as (2) of the above (IV). The difference is that, the precursor of Zn is changed for the corresponding precursor of Fe or Co, which is one of ferric nitrate, ferric chloride and ferric citrate or one of cobalt nitrate, cobalt chloride and cobalt acetate.

The etching process is the same as the preparation processes of products ZnO 3 and ZnO 5 in step (2) in above (I). The catalyst having a great number of surface oxygen vacancies is synthesized. The surface oxygen vacancies are 77% and 51%.

Corresponding products are defined as spinel 6 and spinel 7.

(VI) $Cr_2O_3$, $Al_2O_3$ or $ZrO_2$ dispersed active metal oxide $Cr_2O_3$, $Al_2O_3$ or $ZrO_2$ dispersed active metal oxide is prepared through a precipitate deposition method by taking $Cr_2O_3$, $Al_2O_3$ or $ZrO_2$ as carriers. Taking preparation of oxide by dispersed ZnO as an example, commercial $Cr_2O_3$, $Al_2O_3$ or $ZrO_2$ carrier is dispersed in a base solution in advance, and then mixed and precipitated at room temperature with a sodium hydroxide precipitant by taking zinc nitrate as raw material. The molar concentration of $Zn^{2+}$ is 0.067M; and the ratio of molar fractions of $Zn^{2+}$ and the precipitant is 1:8; and then aging is conducted at 160° C. for 24 hours to obtain carrier $Cr_2O_3$, $Al_2O_3$ or $ZrO_2$ dispersed ZnO oxide (the contents of the dispersing agents in catalyst A are 0.1 wt %, 10 wt % and 90 wt %).

The etching process is the same as the preparation processes of products ZnO 3, ZnO 5 and ZnO 8 in step (2) in above (I). The catalyst having a great number of surface oxygen vacancies is synthesized. The surface oxygen vacancies are 65%, 30% and 25%. The aftertreatment process is the same as step (3) in above (I).

Corresponding products from top to bottom are defined as dispersed oxides 1-3.

The same method is used to obtain carrier $Cr_2O_3$, $Al_2O_3$ or $ZrO_2$ dispersed MnO oxide (the contents of the dispersing agents in catalyst A are 5 wt %, 30 wt % and 60 wt %). The surface oxygen vacancies are 62%, 27% and 28%. Corresponding products from top to bottom are defined as dispersed oxides 4-6.

II. Preparation of Zeolite Having MEL Topology, i.e., Component B:

1) The specific preparation process is as follows:

The preparation of the MEL zeolite:

NaOH, $NaAlO_2$, silica sol, TBABr and water are weighed successively in the proportion of $2.9Na_2O:1Al_2O_3$: $9TBABr:30SiO_2:1260H_2O$, stirred for 3 h, then transferred into a hydrothermal reactor and sealed in 90 rpm selection oven at 150° C. for 3 days.

Then, the materials are centrifugally washed, dried and roasted, subjected to ion exchange with IM ammonium nitrate solution at 70° C. for 8 h, washed with water, filtered, dried, and roasted at 540° C. for 6 h to obtain an MEL zeolite product.

III. Catalyst Preparation

The component A and the component B in the required ratio are added to the container to achieve the purposes of separation, crushing, uniform mixing and the like through one or more than two of extrusion force, impact force, shear force and friction force generated by high-speed motion of the material and/or the container, so as to realize conversion of mechanical energy, thermal energy and chemical energy by regulating the temperature and the atmosphere of carrier gas, thereby further enhancing the interaction between different components.

In the mechanical mixing process, the mixing temperature can be set as 20-100° C., and the mechanical mixing process can be conducted in an atmosphere or directly in the air. The atmosphere is one or more than one of: a) nitrogen and/or inert gas; b) mixed gas of hydrogen, nitrogen and/or inert gas, with the volume ratio of hydrogen in the mixed gas being 5-50%; c) mixed gas of carbon monoxide, nitrogen and/or inert gas, with the volume ratio of carbon monoxide in the mixed gas being 5-20%; and d) mixed gas of oxygen, nitrogen and/or inert gas, with the volume ratio of oxygen in the mixed gas being 5-20%. The inert gas is one or more than one of helium, argon and neon.

Mechanical stirring: mixing the component A and the component B with a stirring rod in a stirring tank; and regulating the mixing degree and the relative distance of the component A and the component B by controlling stirring time (5 min-120 min) and rate (30-300 r/min).

Ball milling: Rolling at high speed in a grinding tank by using abrasive and the catalysts; and producing strong impact and milling on the catalysts to achieve the effects of dispersing and mixing the component A and the component B. The ratio of the abrasive (which is stainless steel, agate and quartz; and the size range is 5 mm-15 mm) to the catalysts (the mass ratio scope is 20-100:1) is controlled to regulate the particle size and the relative distance of the catalysts.

Shaking table mixing: premixing the component A and the component B and placing the catalysts into the container; realizing the mixing of the component A and the component B by controlling the reciprocating oscillation or circumferential oscillation of a shaking table; and realizing uniform mixing and regulating the relative distance by regulating oscillation speed (range: 1-70 r/min) and time (range: 5 min-120 min).

Mechanical grinding: premixing the component A and the component B and placing the catalysts into the container; and under certain pressure (range: 5 kg-20 kg), making relative motion (speed range: 30-300 r/min) by the ground and mixed catalysts to achieve the effects of regulating the particle size and the relative distance of the catalysts and realizing uniform mixing.

Specific catalyst preparation and parameter features are shown in Table 6.

TABLE 5

Preparation of Catalysts and Parameter Features

| Catalyst Number | Catalyst Component A | Catalyst Component B | Mass Ratio of A to B | Mechanical Agitation Rate (r/min) and Time (min) | Ball Milling Abrasive Material, Size Range and Catalyst Mass Ratio | Rocking Bed Oscillation Speed (r/min) and Time (min) | Mechanical Polishing Pressure (kg) and Relative Movement Rate (r/min) | Geometrical Center Distance of A and B Particles |
|---|---|---|---|---|---|---|---|---|
| A | ZnO1 | MEL | 0.33 | 5, 3 | | | | 10 mm |
| B | ZnO 2 | MEL | 0.5 | 100, 250 | | | | 200 μm |
| C | spinel 3 | MEL | 2 | | 5 mm stainless steel ball, 80:1 | | | 52 μm |
| D | ZnO4 | MEL | 1 | | 6 mm stainless steel ball, 90:1 | | | 30 nm |
| E | ZnO 5 | MEL | 1 | | | 5, 4 | | 8 mm |
| F | ZnO 6 | MEL | 3 | | | 60, 100 | | 300 μm |
| G | ZnO7 | MEL | 3 | | | | 5, 30 | 100 μm |
| H | ZnO8 | MEL | 1 | 200, 300 | | | | 200 nm |
| I | spinel 1 | MEL | 5 | | 6 mm agate ball, 100:1 | | | 30 μm |
| J | spinel 2 | MEL | 1 | | | 150, 100 | | 500 nm |
| K | spinel 3 | MEL | 3 | | | | 15, 200 | 150 μm |
| L | spinel 4 | MEL | 0.33 | | | | 20, 300 | 70 μm |
| M | spinel 5 | MEL | 1 | 100, 300 | | | | 200 μm |
| N | spinel 6 | MEL | 3 | | 6 mm quartz, 50:1 | | | 800 μm |
| O | spinel 7 | MEL | 0.33 | | 6 mm quartz, 300:1 | | | 40 nm |
| P | MnO 1 | MEL | 1 | | | | 10, 100 | 100 μm |
| Q | MnO 2 | MEL | 1 | | | 5, 10 | | 1 mm |
| R | MnO 3 | MEL | 3 | | | 60, 100 | | 3 mm |
| S | CeO1 | MEL | 3 | | | | 50, 30 | 200 nm |
| T | CeO2 | MEL | 1 | 100, 300 | | | | 300 μm |
| U | CeO3 | MEL | 0.33 | | 6 mm quartz, 100:1 | | | 10 μm |
| V | Cr2O3-1 | MEL | 2 | | | | 5, 30 | 100 μm |
| W | Cr2O3-2 | MEL | 1 | 100, 300 | | | | 400 μm |
| X | Cr2O3-3 | MEL | 0.5 | | 6 mm quartz, 100:1 | | | 15 μm |
| Y | dispersed oxide 1 | MEL | 1 | 10, 20 | | | | 6 mm |
| Z | dispersed oxide 2 | MEL | 3 | | 5 mm stainless steel ball, 200:1 | | | 20 nm |
| Z1 | dispersed oxide 3 | MEL | 1 | | | | 10, 100 | 60 μm |
| Z2 | dispersed oxide 4 | MEL | 4 | | | 30, 60 | | 700 μm |
| Z3 | dispersed oxide 5 | MEL | 3 | | | | 10, 100 | 70 μm |
| Z4 | dispersed oxide 6 | MEL | 20 | | 5 mm stainless steel ball, 100:1 | | | 5 μm |
| Z5 | MnO 1 | MEL | 16 | 100, 200 | | | | 100 μm |
| Z6 | ZnO 1 | MEL | 0.1 | | | | 20, 100 | 200 μm |
| Z7 | dispersed oxide 1 | MEL | 1 | | | | 20, 300 | 60 μm |
| Z8 | spinel 1 | MEL | 1.5 | 60, 100 | | | | 2 mm |
| Z9 | ZnO1 | MEL | 4 | | 5 mm stainless steel ball, 50:1 | | | 5 μm |

TABLE 5-continued

Preparation of Catalysts and Parameter Features

| | | | | Compounding Mode and Condition | | | | |
|---|---|---|---|---|---|---|---|---|
| Catalyst Number | Catalyst Component A | Catalyst Component B | Mass Ratio of A to B | Mechanical Agitation Rate (r/min) and Time (min) | Ball Milling Abrasive Material, Size Range and Catalyst Mass Ratio | Rocking Bed Oscillation Speed (r/min) and Time (min) | Mechanical Polishing Pressure (kg) and Relative Movement Rate (r/min) | Geometrical Center Distance of A and B Particles |
| Z10 | MnO 1 | MEL | 4.5 | | | 50, 120 | | 200 μm |
| Z11 | dispersed oxide 1 | MEL | 2.5 | | | | 100, 200 | 100 nm |
| Z12 | spinel 1 | MEL | 3 | | | | 20, 200 | 50 μm |
| Comparison 1 | ZnO 9 | MEL | 3 | | | 20, 30 | | 10 mm |
| Comparison 2 | Zn 10 | MEL | 2 | 60, 100 | | | | 200 μm |

Example of Catalytic Reactions

A fixed bed reaction is taken as an example, but the catalyst is also applicable to a fluidized bed reactor. The apparatus is equipped with gas mass flow meters and online product analysis chromatography (the tail gas of the reactor is directly connected with the metering valve of chromatography, and thus periodic and real-time sampling and analysis will be achieved).

The above catalyst in the present invention is placed in a fixed bed reactor. The air in the reactor is replaced with Ar; and then the temperature is raised to 300° C. in the $H_2$ atmosphere, and then the syngas ($H_2$/CO molar ratio=0.2-3.5) is switched. The pressure of the syngas is 0.5-10 MPa. The temperature is raised to reaction temperature of 300-600° C., and the air velocity of the reaction raw gas is regulated to 500-8000 ml/g/h. On-line chromatography is used to detect and analyze the product.

1. The reaction performance can be changed by changing the temperature, pressure and space velocity. The selectivity of the gasoline fraction in the product is high and can reach 50-80%. The other products are mainly light olefins with high added value, and the selectivity of the light olefins can reach 10-30%.

Compared with the traditional Fischer-Tropsch synthesis technology, the selectivity of the methane byproduct is low, which is less than 10%. The gasoline composition comprises a large amount of iso-hydrocarbons with high octane value and aromatic hydrocarbons; and the linear hydrocarbons have low selectivity and high oil quality.

TABLE 6

Application and Effect of Catalysts

| Embodiments | Catalyst | GHSV ($h^{-1}$) | Temperature (° C.) | $H_2$/CO Molar Ratio | Pressure (MPa) | Hydrocarbon Space Time Yield g Olefin/hg Catalyst | Gasoline Selectivity % | $CH_4$ Selectivity % | Light Olefin Selectivity % | Oxygen Hole 40 50 |
|---|---|---|---|---|---|---|---|---|---|---|
| 1 | A | 1000 | 360 | 2.5 | 2 | 0.2 | 51 | 9 | 28 | 21% |
| 2 | B | 1000 | 360 | 3 | 4 | 0.7 | 67 | 5 | 14 | 45% |
| 3 | C | 600 | 370 | 2.5 | 3.5 | 1.5 | 73 | 3 | 18 | 73% |
| 4 | D | 1600 | 350 | 1 | 10 | 1.3 | 78 | 2 | 11 | 67% |
| 5 | E | 1400 | 370 | 3 | 1 | 0.6 | 55 | 10 | 25 | 30% |
| 6 | F | 2500 | 390 | 0.5 | 3 | 1.3 | 70 | 4 | 15 | 52% |
| 7 | G | 3000 | 375 | 2.5 | 2.5 | 0.6 | 60 | 7 | 25 | 22% |
| 8 | H | 500 | 380 | 2 | 3.5 | 0.7 | 67 | 7 | 18 | 29% |
| 9 | I | 1100 | 340 | 2.5 | 3.5 | 0.5 | 63 | 6 | 20 | 41% |
| 10 | J | 500 | 330 | 1 | 8 | 1.5 | 77 | 2 | 11 | 72% |
| 11 | K | 3100 | 430 | 0.5 | 3 | 1.9 | 71 | 2 | 11 | 83% |
| 12 | L | 7000 | 520 | 1.5 | 3.5 | 0.3 | 65 | 5 | 15 | 20% |
| 13 | M | 1000 | 450 | 0.3 | 9 | 0.6 | 65 | 6 | 21 | 24% |
| 14 | N | 1000 | 310 | 1 | 3.5 | 0.6 | 67 | 4 | 20 | 77 |
| 15 | O | 800 | 350 | 1 | 4.5 | 0.5 | 65 | 5 | 18 | 51 |
| 16 | P | 2000 | 470 | 1.5 | 3.5 | 1.9 | 74 | 3 | 11 | 56 |
| 17 | Q | 3600 | 450 | 2 | 4 | 0.8 | 52 | 10 | 24 | 36 |
| 18 | R | 5500 | 470 | 2 | 3 | 0.3 | 52 | 10 | 25 | 27 |
| 19 | S | 700 | 330 | 1 | 5.5 | 1.9 | 76 | 2 | 11 | 67 |
| 20 | T | 6000 | 440 | 1.5 | 5 | 0.6 | 61 | 5 | 22 | 38 |
| 21 | U | 1800 | 330 | 1 | 6.5 | 0.3 | 67 | 7 | 27 | 25 |
| 22 | V | 1500 | 450 | 1.5 | 7 | 0.9 | 64 | 7 | 22 | 45 |
| 23 | W | 1500 | 400 | 0.5 | 4 | 0.4 | 66 | 6 | 24 | 29 |
| 24 | X | 3000 | 400 | 1 | 5 | 0.4 | 60 | 7 | 25 | 20 |
| 25 | Y | 500 | 360 | 0.5 | 5 | 0.8 | 61 | 7 | 25 | 65 |
| 26 | Z | 1500 | 350 | 1.5 | 5 | 0.4 | 50 | 10 | 27 | 30 |
| 27 | Z1 | 2500 | 410 | 2.5 | 6 | 0.7 | 67 | 6 | 25 | 25 |
| 28 | Z2 | 4000 | 420 | 3 | 2 | 1.3 | 63 | 5 | 24 | 62 |
| 29 | Z3 | 3000 | 430 | 3.5 | 8 | 0.4 | 65 | 7 | 19 | 27 |
| 30 | Z4 | 5000 | 390 | 3 | 2.5 | 0.5 | 53 | 8 | 26 | 28 |

TABLE 6-continued

Application and Effect of Catalysts

| Embodiments | Catalyst | GHSV ($h^{-1}$) | Temperature (°C.) | $H_2/CO$ Molar Ratio | Pressure (MPa) | Hydrocarbon Space Time Yield g Olefin/hg Catalyst | Gasoline Selectivity % | $CH_4$ Selectivity % | Light Olefin Selectivity % | Oxygen Hole |
|---|---|---|---|---|---|---|---|---|---|---|
| 31 | Z5 | 2000 | 410 | 3.5 | 1.5 | 1.4 | 57 | 5 | 28 | 56 |
| 32 | Z6 | 2000 | 470 | 0.3 | 10 | 0.4 | 54 | 8 | 27 | 21 |
| 33 | Z7 | 2000 | 340 | 3.5 | 1 | 1.7 | 78 | 5 | 10 | 65 |
| 34 | Z8 | 1000 | 410 | 3 | 3 | 0.7 | 51 | 8 | 25 | 41 |
| 35 | Z9 | 500 | 360 | 3.5 | 4 | 0.5 | 66 | 7 | 24 | 21 |
| 36 | Z10 | 4200 | 410 | 2 | 3 | 1.7 | 78 | 5 | 10 | 56 |
| 37 | Z11 | 1000 | 350 | 3.5 | 2 | 1.9 | 79 | 4 | 10 | 65 |
| 38 | Z12 | 2000 | 420 | 3 | 4 | 0.8 | 59 | 6 | 29 | 41 |
| 39 | Reference example 1 | 3000 | 320 | 0.5 | 1 | 0.07 | 19 | 11 | 18 | |
| 40 | Reference example 2 | 2000 | 450 | 1 | 2 | 1.0 | 27 | 31 | 12 | |
| 41 | Reference example 3 | 4000 | 450 | 3 | 3 | 1.0 | 37 | 47 | 13 | |
| 42 | Reference example 4 | 3000 | 350 | 2.5 | 3 | 0.06 | 2 | 64 | 27 | |
| 43 | Reference example 5 | 5000 | 450 | 1 | 4 | 0.7 | ~ | 9 | 50 | |
| 44 | Reference example 6 | 2000 | 410 | 2 | 3.5 | 0.15 | ~ | 80 | 11 | |
| 45 | Reference example 7 | 3000 | 410 | 2.5 | 4 | 0.3 | 5 | 51 | 22 | |
| 46 | Reference example 8 | 3200 | 410 | 3 | 2 | 2 | 41 | 42 | 11 | |
| 47 | Reference example 9 | 20000 | 290 | 2 | 5.1 | 1.0 | 29 | 12 | 15 | |

ZnO in the catalyst in reference example 1 has no oxygen vacancy, and thus the activity is low.

ZnO in the catalyst in reference example 2 is completely reduced into a metallic state, resulting in high selectivity of the methane in the product.

The catalyst adopted in reference example 3 comprises metal ZnCo of the component A and MEL of the component B. The molar ratio of ZnCo is 1:1. The mass ratio of ZnCo to MEL is 1:1. Other parameters and the mixing process are the same as those of catalyst A.

The component A of the catalyst adopted in reference example 4 is MgO without surface oxygen vacancy, and the component B is MEL. Other parameters and the mixing process are the same as those of catalyst A.

The zeolite in the catalyst adopted in reference example 5 is a commodity SAPO-34 purchased from Nankai University Catalyst Factory.

The zeolite in the catalyst adopted in reference example 6 is a small pore zeolite having LEV structure.

The distance between the metal oxide and the zeolite in the catalyst adopted in reference example 7 is 30 mm. Other parameters and the mixing process are the same as those of catalyst A.

The metal oxide in the catalyst adopted in reference example 8 is located in porous channels of the zeolite and is in close contact with the porous channels. Other parameters and the like are the same as those of catalyst A.

A carbon nanotube-limited iron catalyst is adopted in reference example 9, wherein iron load is 10%, and the selectivity of the $C_{5+}$ product in the hydrocarbon is 29%.

Explanation of Reaction Results:

Explanation I:

Reaction results of reference examples 5 and 6 show that, the topology is crucial to the selective modulation of the products; SAPO34 structure is suitable for production of $C_2$-$C_4$ hydrocarbons; $C_3$ hydrocarbon products are the most; LEV structure is suitable for production of the methane.

The MEL zeolite used by the present invention has ten-membered ring orifices and a three-dimensional porous channel structure shows the special benefits not owned by zeolites of other structures. The product mainly comprises the gasoline fraction, and the content of iso-paraffins is high. At the same time, light olefins are cogenerated.

Explanation II:

The distance between the metal oxide and the zeolite in the catalyst adopted in reference example 7 is 30 mm. Other parameters and the mixing process are the same as those of catalyst A.

The metal oxide in the catalyst adopted in reference example 8 is located in porous channels of the zeolite and is in close contact with the porous channels. Other parameters and the like are the same as those of catalyst A.

Reaction results of reference examples 7 and 8 show that, long distance and short distance lead to high selectivity of the methane, and are not conducive to the production of the gasoline fraction.

It is observed from the above table that the structure of the zeolite including the topologies, and the matching of the distance between the metal oxide and the zeolite are crucial and directly affect the selectivity of the gasoline fraction and the light olefins.

Reaction results of reference examples 7 and 8 show that, long distance and short distance lead to high selectivity of the methane, and are not conducive to the production of the gasoline fraction.

It is observed from the above table that the structure of the zeolite including the topologies of MEL, and the matching of the distance between the metal oxide and the zeolite are crucial and directly affect the selectivity of the gasoline fraction and the light olefins.

The invention claimed is:

1. A catalyst comprising component A and component B, wherein the component A comprises a metal oxide selected from MnO, $Cr_2O_3$, ZnO, $CeO_2$, $MnCr_2O_4$, $MnAl_2O_4$, $MnZrO_4$, $ZnCr_2O_4$, $ZnAl_2O_4$, $CoAl_2O_4$, $FeAl_2O_4$, and mixtures thereof,
wherein the component B comprises a zeolite having a MEL structure,
wherein the metal oxide has oxygen vacancies at an oxygen vacancy concentration of 20-90%, and wherein the oxygen vacancy concentration equals 100% less a percentage of a weight of oxygen atoms in the metal oxide in a weight of a stoichiometric amount of oxygen atoms in the metal oxide.

2. The catalyst according to claim 1, wherein the catalyst component A is one or more metal oxides selected from MnO, $Cr_2O_3$, $MnCr_2O_4$, $MnAl_2O_4$, $MnZrO_4$, $ZnAl_2O_4$, $CeO_2$, $CoAl_2O_4$, and $FeAl_2O_4$,
the zeolite having MEL structure is composed of H, O, Si and Al, and the component B optionally comprises one or more dispersing agents selected from $Al_2O_3$, graphite, $SiO_2$, $ZrO_2$, $TiO_2$, $Cr_2O_3$, $Ga_2O_3$, CaO, MgO, $CeO_2$, $In_2O_3$, and $SnO_2$, and wherein a content of the dispersing agents is 0-50% wt of a total weight of the component B.

3. The catalyst according to claim 1, wherein a distance between a geometric center of the metal oxide in the component A and the zeolite particle in the component B is 20 nm-10 mm.

4. The catalyst according to claim 1, wherein a weight ratio of the metal oxide in the component A to the component B is within a range of 0.1-20 times.

5. The catalyst according to claim 1, wherein the metal oxide is in form of crystals having a size of 5-30 nm, and the oxygen vacancies reside within a depth of 0.3 nm from a surface of the crystals.

6. The catalyst according to claim 1, wherein the component A comprises a dispersing agent selected from $Al_2O_3$, $Cr_2O_3$, $ZrO_2$, and $TiO_2$, and a content of the dispersing agent in the component A is 10-90 wt %.

7. A method for preparing liquid fuels and light olefins by direct conversion of syngas, comprising contacting a syngas with a catalyst of claim 1 comprising component A and component B,
wherein the component A comprises a metal oxide selected from MnO, $Cr_2O_3$, $CeO_2$, ZnO, $MnCr_2O_4$, $MnAl_2O_4$, $MnZrO_4$, $ZnCr_2O_4$, $ZnAl_2O_4$, $CoAl_2O_4$, $FeAl_2O_4$, and mixtures thereof, wherein the component B comprises a zeolite having a MEL structure.

8. The method according to claim 7, wherein a pressure of the syngas is 0.1-10 MPa, a reaction temperature is 300-600° C., and a space velocity of the syngas is 300-10000 $h^{-1}$.

9. The method according to claim 7, wherein a molar ratio of $H_2$ to CO in the syngas 0.2-3.5.

10. The catalyst according to claim 2, wherein the component A is selected from MnO, $Cr_2O_3$, $MnCr_2O_4$, $MnAl_2O_4$, $MnZrO_4$, $CeO_2$, $CoAl_2O_4$, $FeAl_2O_4$, and mixtures thereof.

11. The catalyst according to claim 3, wherein the distance between geometric center of the metal oxide of the component A and the geometric center of the zeolite particle in the component B is 100 nm-0.5 mm.

12. The catalyst according to claim 4, wherein the weight ratio of the metal oxide in the component A to the component B is 0.3-5.

13. The catalyst according to claim 5, wherein the oxygen vacancy concentration is 50-90%.

14. The method according to claim 8, wherein the pressure of the syngas is 2-8 MPa.

15. The method according to claim 8, wherein the reaction temperature is 300° C.-500° C.

16. The method according to claim 9, wherein the molar ratio of $H_2$ to CO in the syngas 0.3-2.5.

17. The catalyst of claim 1, wherein the component A and the component B are mixed by stirring, ball milling, shaking table mixing, or grinding.

18. A catalyst comprising component A and component B, wherein the component A comprises a metal oxide selected from MnO, $Cr_2O_3$, $CeO_2$, $MnCr_2O_4$, $MnAl_2O_4$, $MnZrO_4$, $ZnCr_2O_4$, $ZnAl_2O_4$, $CoAl_2O_4$, $FeAl_2O_4$, and mixtures thereof, and the component B comprises a zeolite having a MEL structure, wherein the metal oxide has oxygen vacancies at an oxygen vacancy concentration of 20-90%, and wherein the oxygen vacancy concentration equals 100% less a percentage of a weight of oxygen atoms in the metal oxide in a weight of a stoichiometric amount of oxygen atoms in the metal oxide.

19. The catalyst of claim 18, consisting of the component A and the component B.

* * * * *